United States Patent
Kuenstner

(10) Patent No.: US 10,292,995 B2
(45) Date of Patent: May 21, 2019

(54) TREATMENT OF DISEASES USING COMBINATION OF ULTRAVIOLET BLOOD IRRADIATION AND ANTIBIOTICS

(71) Applicant: John Todd Kuenstner, Charleston, WV (US)

(72) Inventor: John Todd Kuenstner, Charleston, WV (US)

( * ) Notice: Subject to any disclaimer, the term of this patent is extended or adjusted under 35 U.S.C. 154(b) by 0 days.

(21) Appl. No.: 15/707,194

(22) Filed: Sep. 18, 2017

(65) Prior Publication Data

US 2018/0028551 A1 Feb. 1, 2018

Related U.S. Application Data

(63) Continuation of application No. 14/720,354, filed on May 22, 2015.

(60) Provisional application No. 62/002,141, filed on May 22, 2014.

(51) Int. Cl.

| | | |
|---|---|---|
| A61K 31/7048 | (2006.01) | |
| A61K 31/435 | (2006.01) | |
| A61K 31/07 | (2006.01) | |
| A61K 31/59 | (2006.01) | |
| A61K 45/06 | (2006.01) | |
| A61M 1/36 | (2006.01) | |
| A61K 31/133 | (2006.01) | |
| A61K 31/438 | (2006.01) | |
| A61K 31/496 | (2006.01) | |
| A61K 31/498 | (2006.01) | |
| A61K 31/5383 | (2006.01) | |
| A61N 5/06 | (2006.01) | |

(52) U.S. Cl.
CPC .......... *A61K 31/7048* (2013.01); *A61K 31/07* (2013.01); *A61K 31/133* (2013.01); *A61K 31/435* (2013.01); *A61K 31/438* (2013.01); *A61K 31/496* (2013.01); *A61K 31/498* (2013.01); *A61K 31/5383* (2013.01); *A61K 31/59* (2013.01); *A61K 45/06* (2013.01); *A61M 1/3681* (2013.01); *A61M 2205/053* (2013.01); *A61N 5/0624* (2013.01); *A61N 2005/0661* (2013.01)

(58) Field of Classification Search
CPC ................................................ A61K 31/7048
See application file for complete search history.

(56) References Cited

PUBLICATIONS

Borody, Anti-mycobacterial therapy in Crohn's disease heals mucosa with longitudinal scars, Digestive and Liver Disease 39 (2007) 438-444.*
Baumgart, Crohn's disease, The Lancet, vol. 380, Issue 9853, Nov. 3-9, 2012, pp. 1590-1605.*
Greenstein, Vitamins A & D Inhibit the Growth of Mycobacteria in Radiometric Culture, PLoS One, Published: Jan. 3, 2012.*
Chamberlin, Blood cultures of 19 Crohn's disease patients, American Journal of Gastroenterology, Mar. 2008; 103(3) 802-803.*
NCT00056355, Extracorporeal Photopheresis to Maintain Symptoms Remission During Steroid Withdrawal in Patients With Steroid-Dependent Crohn's Disease, updated Mar. 3, 2008.*

* cited by examiner

*Primary Examiner* — Svetlana M Ivanova
(74) *Attorney, Agent, or Firm* — Spilman Thomas & Battle PLLC; William P. Smith

(57) ABSTRACT

A method of and composition for treating a patient having *Mycobacterium avium* complex (MAC), and in one embodiment *Mycobacterium avium* subspecies *paratuberculosis* (MAP), causing one or more diseases, an embodiment of the method including administering to the patient an effective amount of one or more antibiotics and administering to the patient an effective amount of ultraviolet blood irradtiation (UVBI) treatments, and an embodiment of the composition including an effective amount of one or more antibiotics and an effective amount of UVBI treated blood of the patient.

30 Claims, 1 Drawing Sheet

TREATMENT OF DISEASES USING COMBINATION OF ULTRAVIOLET BLOOD IRRADIATION AND ANTIBIOTICS

CROSS REFERENCE TO RELATED APPLICATION

This application is a continuation of U.S. patent application Ser. No. 14/720,354, filed May 22, 2015, which claims priority to U.S. Provisional Patent Application No. 62/002,141, filed May 22, 2014, both of which are incorporated herein in by reference in their entireties.

FIELD OF THE INVENTION

This invention is related to the treatment of diseases, and more particularly to the treatment of *Mycobacterium avium* complex (MAC), and in an embodiment *Mycobacterium avium* subspecies *paratuberculosis* (MAP), causing one or more diseases using a combination of antibiotics and/or ultraviolet blood irradiation (UVBI).

BACKGROUND OF THE INVENTION

*Mycobacterium avium* subspecies *paratuberculosis* (MAP) is a bacterium that causes Johne's disease, a chronic diarrheal wasting disease in cattle and a chronic wasting disease in sheep and goats. This bacterium has long been suspected to cause Crohn's disease. A diarrheal/wasting illness associated with infection with MAP has also been reported in non-human primates. The viable bacterium is found in commercially available pasteurized milk. In fact, 2.7% of retail pasteurized milk samples purchased in Wisconsin, Minnesota and California were found to contain viable MAP. Because of the prevalence of this organism in the food chain and because Johne's disease is a worldwide zoonosis, it should not be surprising that the first mass screening of the human population in a study done in North India on 26,390 serum samples submitted for multiple medical conditions including diabetes, liver disorders, anemia, thyroid, tuberculosis, typhoid, abdominal disorders, inflammatory illness and ion imbalance, showed that 34% of the samples had evidence of MAP infection by an ELISA antibody test. The same study showed that 12.7% of apparently normal individuals had IS900 PCR evidence of MAP in their blood.

Once an animal is infected, the MAP bacterium grows and multiplies inside the cells of the immune system. The organism is excreted in the feces, and to a lesser extent in milk. Outside the host animal, the bacterium multiplies poorly, but can survive over a year in the environment because of its resistance to heat, cold and the effect of drying. This slow-growing bacterium affects the ileum and causes diarrhea and cachexia. There is no known curative treatment for Johne's disease.

It has been suggested that there may be an association between Crohn's disease (CD) and Johne's disease. Studies have shown an increase in the detection and isolation of MAP in adult Crohn's patients and in children newly diagnosed with Crohn's disease, and that most patients with Crohn's disease may have MAP. Crohn's disease, like Johne's disease, has been treated with antibiotic therapy. However, patients undergoing such treatment for Crohn's disease may have a significant relapse rate and thus such treatments may not be optimal. Favorable results in the treatment of Crohn's disease using conventional therapies may be only around 30 percent.

Therefore, there may be a need for a different and/or more expanded therapy that may be more effective than conventional methods in fighting Crohn's disease and other diseases.

SUMMARY OF THE INVENTION

In an embodiment, a method of treating a patient having *Mycobacterium avium* complex (MAC) causing one or more diseases includes: administering to the patient an effective amount of one or more antibiotics; and administering to the patient an effective amount of ultraviolet blood irradiation (UVBI) treatment.

In another embodiment, a method of treating a patient having *Mycobacterium avium* complex (MAC) causing one or more diseases includes: administering to a patient an effective amount of ultraviolet blood irradiation (UVBI) treatment; and taking repeated measurements of MAC in the patient to demonstrate eradication of the MAC in the patient.

In another embodiment, a composition for treating a patient having *Mycobacterium avium* complex (MAC) causing one or more diseases includes: an effective amount of one or more antibiotics; and an effective amount of ultraviolet blood irradiation (UVBI) treated blood of the patient.

In another embodiment, a composition for treating a patient having *Mycobacterium avium* complex (MAC) causing one or more diseases includes: an effective amount of ultraviolet blood irradiation (UVBI) treated blood of the patient.

In another embodiment, a method of treating a patient having *Mycobacterium avium* subspecies *paratuberculosis* (MAP) causing one or more autoimmune diseases includes: administering to the patient an effective amount of one or more antibiotics; and administering to the patient an effective amount of ultraviolet blood irradiation (UVBI) treatment.

In another embodiment, a method of treating a patient having *Mycobacterium avium* subspecies *paratuberculosis* (MAP) causing one or more autoimmune diseases includes: administering to a patient an effective amount of ultraviolet blood irradiation (UVBI) treatment; and taking repeated measurements of MAP to demonstrated eradication of the MAP.

In another embodiment, a composition for treating a patient having *Mycobacterium avium* subspecies *paratuberculosis* (MAP) causing one or more autoimmune diseases includes: an effective amount of one or more antibiotics; and an effective amount of ultraviolet blood irradiation (UVBI) treated blood of the patient.

In another embodiment, a composition for treating a patient having *Mycobacterium avium* subspecies *paratuberculosis* (MAP) causing one or more autoimmune diseases includes: an effective amount of ultraviolet blood irradiation (UVBI) treated blood of the patient.

BRIEF DESCRIPTION OF THE DRAWINGS

The accompanying drawings are included to provide a further understanding of embodiments of the invention, are incorporated in and constitute a part of this specification, and together with the description serve to explain the principles of embodiments of the invention.

Various other objects, features and advantages of the invention will be readily apparent according to the following description exemplified by the drawings, which are shown by way of example only, wherein.

DETAILED DESCRIPTION

Figure 1:
FIG. 1 shows the terminal ileum of the patient from Example 1 herein with multiple ulcers.

Reference will now be made to embodiments of compositions and methods for treating *Mycobacterium avium* complex (MAC), and in embodiments *Mycobacterium avium* subspecies *paratuberculosis* (MAP), causing one or more diseases. Details, features, and advantages of the treatment compositions and methods will become further apparent in the following detailed description of embodiments thereof.

Any reference in the specification to "one embodiment," "a certain embodiment," or a similar reference to an embodiment is intended to indicate that a particular feature, structure or characteristic described in connection with the embodiment is included in at least one embodiment of the invention. The appearances of such terms in various places in the specification do not necessarily all refer to the same embodiment. References to "or" are furthermore intended as inclusive, so "or" may indicate one or another of the ored terms or more than one ored term.

As used herein, the term "effective amount" refers to that amount of a substance desired to bring about a desired effect in a patient. Regarding autoimmune diseases as described herein, the "effective amount" refers to the amount of a substance to treat one or more of the autoimmune diseases and MAP. Regarding diseases as described herein with respect to MAC, the "effective amount" refers to the amount of a substance to treat one or more of the diseases and MAC. As used herein, the term "patient" refers to any member of the animal kingdom, including but not limited to animals and *homo sapiens*.

Accordingly, embodiments of the present invention include a method for treating a patient having one or more autoimmune diseases comprising using ultraviolet blood irradiation (UVBI) and one or more antibiotics such as, in various embodiments, one or more of clarithromycin, azithromycin, rifampicin, rifabutin, clofazimine, ciprofloxacin, and metronidazole. Other embodiments of the present invention include a composition for treating a patient having one or more autoimmune diseases comprising UVBI treated blood and one or more antibiotics such as, in various embodiments, one or more of clarithromycin, azithromycin, rifampicin, rifabutin, clofazimine, ciprofloxacin, and metronidazole. The composition and method may treat an underlying infection by MAP causing the one or more autoimmune diseases. One or more alternative or additional antibiotics may be used in the method and/or composition. In one embodiment of the method and/or composition, Vitamin A and/or Vitamin D is added to the combination therapy of UVBI and one or more of the aforementioned or other antibiotics.

The UVBI treatment in embodiments of the method of treating a patient having MAP causing one or more autoimmune diseases may include any method of providing UVBI. For example, the UVBI treatment may include inserting a catheter into a vein of a forearm of a patient, removing 200 cc or another amount of blood from the patient, irradiating the removed blood using ultraviolet light, and then returning that blood to the bloodstream of the patient. The irradiation of the blood with ultraviolet light may be by way of passing the blood through a quartz cuvette or other tubing where it is exposed to ultraviolet light. Other UVBI methods and devices may be used in other embodiments. The UVBI treated blood in embodiments of the compositions for treating a patient having MAP causing one or more autoimmune diseases may include UVBI treated blood of the patient from the aforementioned or another UVBI treatment method and/or device.

The one or more autoimmune diseases may include, but are not limited to, one or more of Crohn's disease, ulcerative colitis, type 1 diabetes mellitus, multiple sclerosis, complex regional pain syndrome, hypothyroidism, idiopathic thrombocytopenic purpura, lymphangiomatosis, sarcoidosis, Sjogren's disease, myasthenia gravis, scleroderma, systemic lupus erythematosis, psoriasis, and fibromyalgia.

In another embodiment of the present invention, a method for treating a patient with one or more autoimmune diseases includes providing multiple repeated treatments of UVBI alone for the autoimmune diseases in conjunction with MAP blood cultures and/or MAP antibodies to demonstrate eradication of the organism. In another embodiment, a composition for treating a patient having MAP causing one or more autoimmune diseases includes an effective amount of UVBI treated blood.

In various embodiments, the method of treating MAP causing one or more autoimmune diseases, such as those provided herein, comprises administering to a patient an effective amount of at least one antibiotic and at least one UVBI treatment. For example, the treatment method may include the administration to a patient of at least 18 mg/kg/day of clarithromycin. The method may also or alternatively include administering to the patient at least 11 mg/kg/day of rifabutin or at least 9 mg/kg/day of rifampin. The method may further include administering to the patient at least 14 mg/kg/day of ciprofloxacin or at least 7 mg/kg/day of levofloxacin. The method may include, in one preferred embodiment, concurrently administering to the patient the one or more antibiotics, the administration of the one or more antibiotics also at least partially over the same time period as when the UVBI treatments are administered. In an embodiment, the method may include administering to the patient at least 4 mg/kg per week of clofazimine, such as when the patient is in clinical remission. As used herein, "clinical remission" is the partial or complete disappearance of the clinical and subjective characteristics of the one or more autoimmune diseases provided herein. The method may further include, with any of those antibiotic combinations, administering to the patient UVBI treatment at least once a week for at least 12 weeks. In a preferred embodiment, the method includes starting the patient on the UVBI treatment from about two or more weeks earlier to the time the antibiotics begin to be administered to the patient. In a more preferred embodiment, the antibiotics, such as for example but not limited to clarithromycin, rifabutin or rifampin, and ciprofloxacin or levofloxacin in the effective dosages above are taken for at least two years and up to three years, though in other embodiments other durations of time may be used. In preferred embodiments, when multiple antibiotics are taken, they may be taken concurrently at first and then cycled later, or they may be only taken concurrently, or they may only be cycled.

In various embodiments, a composition for treating a patient for MAP causing one or more autoimmune diseases, such as those provided herein, comprises an effective amount of at least one antibiotic such as provided in the above paragraph and an effective amount of UVBI treated blood of the patient such as provided by the UVBI treatment method of the above paragraph. In one preferred embodiment, the one or more antibiotics may be taken concurrently with respect to each other and also at least partially over the same time period as when the UVBI treated blood is returned to the bloodstream of the patient.

For example, in one embodiment, a method of treating Crohn's disease in a patient includes providing antibiotic therapy, which may include clarithromycin and rifabutin and/or ciprofloxacin, along with UVBI treatment. For example, the patient may take up to 750 mg of clarithromycin a day, and 200 mg twice daily of rifabutin and these antibiotics may be taken concurrently in a preferred embodiment. The patient may additionally receive ultraviolet blood irradiation (UVBI) treatment, such as once weekly UVBI treatments for 11 weeks in one embodiment. In a preferred embodiment, the UVBI treatment is administered at least partially concurrently with the antibiotics. For example, the UVBI treatment may be started two or more weeks before the antibiotics begin to be administered to the patient (and continued during at least some of the time that the antibiotics are administered). In an embodiment, once the patient is in clinical remission from the aforementioned therapy or at another time, clofazimine may be added, such as a dosage of 50 mg per day. The aforementioned dosages of the antibiotics and the UVBI treatment schedule may be different in different embodiments. Different antibiotics may be used in other embodiments. In another embodiment, the patient may also receive Vitamin A and/or Vitamin D in addition to the antibiotics and UVBI.

In an embodiment, a composition for treating Crohn's disease in a patient includes at least one antibiotic, which may include clarithromycin and rifabutin and/or ciprofloxacin, and UVBI treated blood of the patient. For example, the at least one antibiotic may include up to 750 mg of clarithromycin a day, and 200 mg twice daily of rifabutin, and the UVBI treated blood of the patient may include UVBI treated blood from once weekly UVBI treatments for 11 weeks. In one preferred embodiment, the one or more antibiotics may be taken concurrently with respect to each other and also at least partially over the same time period as when the UVBI treated blood is returned to the bloodstream of the patient. If desired, the UVBI treatment may be started two or more weeks before the antibiotics start to be administered (and continued during at least some of the time that the antibiotics are administered), and thus the UVBI treated blood may begin to be returned to the bloodstream of the patient two or more weeks before the antibiotics begin to be taken by the patient. In an embodiment, the composition may further include clofazimine, such as at a dosage of 50 mg per day and provided when the patient is in clinical remission or at another time. Different antibiotics may be used in other embodiments. In another embodiment, the composition further includes Vitamin A and/or Vitamin D in addition to the antibiotics and UVBI treated blood.

One embodiment of the therapies for Crohn's disease and MAP as described above includes performing a blood culture of the patient's blood along with a culture or Polymerase Chain Reaction (PCR) test for MAP, and/or a MAP antibody test performed to confirm that any MAP causing the Crohn's disease has been eradicated.

In an example of another preferred embodiment, a method of treating a patient with complex regional pain syndrome caused by MAP includes providing antibiotic therapy to the patient, which may include for example but not limited to clarithromycin 500 mg twice daily, rifampin 300 mg twice daily, ciprofloxacin 250 mg twice daily, and clofazimine 100 mg three times per week plus at least one UVBI treatment. For example, the patient may receive 12 UVBI treatments and those treatments may be at one UVBI treatment per week intervals for 12 weeks or 3 months. The method may include, in one preferred embodiment, concurrently administering to the patient the one or more antibiotics, the administration of the one or more antibiotics also at least partially over the same time period as when the UVBI treatments are administered. For example, the UVBI treatment may be started two or more weeks before the antibiotics begin to be administered to the patient (and continued during at least some of the time that the antibiotics are administered). In one embodiment, the patient may also receive supplementary Vitamin A and/or Vitamin D. In an embodiment, the patient may have one or more blood cultures for MAP to test for and demonstrate eradication. The patient may also have a PCR test for MAP to demonstrate that the patient is negative for MAP.

In an example of another embodiment, a composition for treating a patient with complex regional pain syndrome caused by MAP includes one or more antibiotics and UVBI treated blood. The one or more antibiotics may include for example but not limited to clarithromycin 500 mg twice daily, rifampin 300 mg twice daily, ciprofloxacin 250 mg twice daily, and clofazimine 100 mg three times per week. The UVBI treated blood may include such blood from 12 UVBI treatments (preferably at one UVBI treatment per week over 12 weeks or 3 months). In one preferred embodiment, the one or more antibiotics may be taken concurrently with respect to each other and also at least partially over the same time period as when the UVBI treated blood is returned to the bloodstream of the patient. If desired, the UVBI treatment may be started two or more weeks before the antibiotics start to be administered (and continued during at least some of the time that the antibiotics are administered), and thus the UVBI treated blood may begin to be returned to the bloodstream of the patient two or more weeks before the antibiotics begin to be taken by the patient. The composition may further include Vitamin A and/or Vitamin D.

The following table is a summary of MAP antibody, PCR, and culture results for Examples 1-5 provided below using the methods of this invention (i.e., "anti-MAP therapy"):

TABLE 1

|  | Example 1 | Example 2 | Example 3 | Example 4 |
|---|---|---|---|---|
| MAP Ab | Day 1 p35-0.25 p36-0.16 | Day 1 ELISA S/P 1.24 | Day 1 ELISA S/P 0.49 | Day 1 ELISA S/P 0.15 |
| MAP PCR | Day 1 negative | Day 1 negative | Day 1 negative | Day 1 negative |
| MAP culture | Day 1 positive | Day 1 negative | Day 1 negative | Day 1 positive |
| MAP Ab | 3 mo 7 d p35-0.5 p36-0.3 | 2 wks ELISA S/P 1.31 | | |
| MAP PCR | 3 mo 7 d negative | 2 wks negative | | |
| MAP culture | 3 mo 7 d positive Anti-MAP therapy started 3 mo 8 d | 2 wks positive Anti-MAP therapy started 1 mo 9 d | Day 5 positive | |
| MAP Ab | 4 mo 9 d p35-0.33 p36-0.22 | 5 mo 11 d ELISA S/P 1.20 | | |
| MAP PCR | 4 mo 9 d negative | 5 mo 11 d negative | | |
| MAP culture | 4 mo 9 d positive | 5 mo 11 d negative | | |
| MAP Ab | 3 y 1 mo 28 d negative | 6 mo 1 d ELISA S/P 1.69 | | |

TABLE 1-continued

|  | Example 1 | Example 2 | Example 3 | Example 4 |
|---|---|---|---|---|
| MAP PCR | 3 y 1 mo 28 d negative | 6 mo 1 d negative |  |  |
| MAP culture | 3 y 1 mo 28 d negative | 6 mo 1 d negative |  |  |
| MAP Ab | 10 y 16 d ELISA S/P 0.67 |  |  |  |
| MAP PCR | 10 y 16 d negative |  |  |  |
| MAP culture | 10 y 16 d negative |  |  |  |

Example 1

Figure 2:
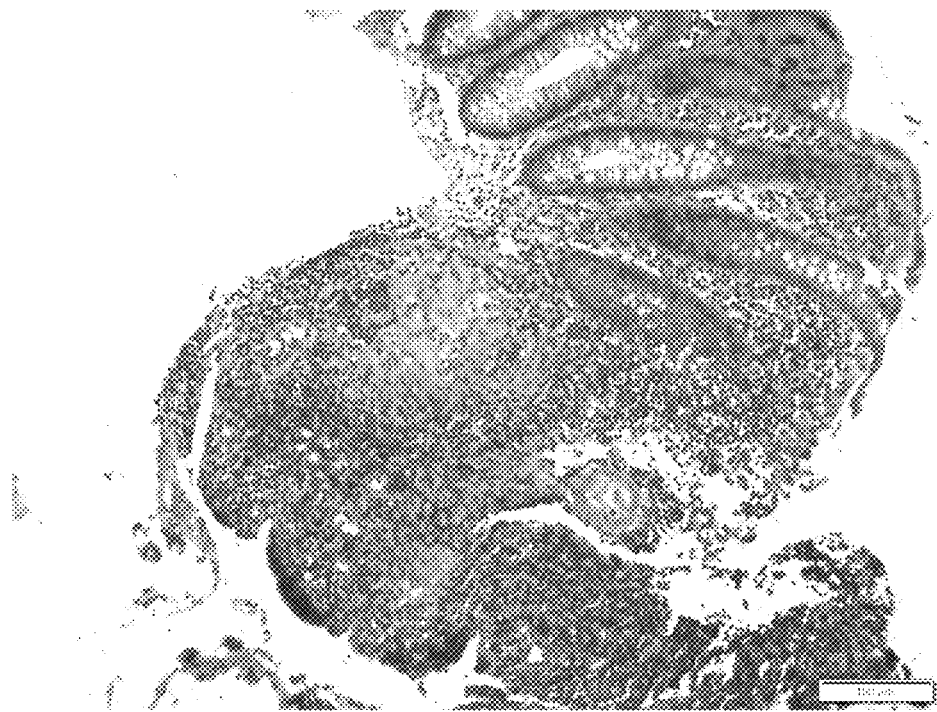
FIG. 2 shows a biopsy from the colon of the patient from Example 1 showing a granuloma of Crohn's disease.

A 9-year-old boy patient was diagnosed with Crohn's disease (CD) a month after day 1 (in which MAP testing was performed as provided in Table 1). He initially presented with persistent diarrhea, weight loss and unexplained fever. His linear growth had slowed considerably. Colonscopy and upper gastrointestinal endoscopy showed multiple aphthous ulcers in the colon, terminal ileum and stomach (see FIG. 1) and biopsies obtained in the colon and gastric antrum contained the granulomas of CD (see FIG. 2). His erythrocyte sedimentation rate (ESR) and C reactive protein (CRP) were increased.

MAP testing was performed on the patient's blood on day 1. The initial sample showed mildly elevated antibody titers to one of the MAP antigens, p35, and after several months of incubation, MAP was grown from the patient's blood. The second sample drawn more than 3 months later showed greater elevations of antibodies to both p35 and p36 antigens and also grew MAP (See Table 1 above for the summary of MAP testing in this and the subsequent 4 cases). During the 3 months between the initial and second sample, the patient's clinical condition steadily worsened with increasing abdominal pain and frequency of diarrhea. At the time of the initial diagnosis, the patient was 4 feet 8.75 inches or in the 95th percentile in stature and weighed 71.8 pounds (75th percentile). Prior to the onset of illness, his weight had previously reached 80 pounds (90th percentile). Initially, three months after day 1, the patient received azathioprine and steroids with concurrent antibiotic therapy including clarithromycin and rifabutin, in low doses (e.g. clarithromycin about or near 750 mg per day and rifabutin about or near 450 mg per day). The patient also took daily probiotics, which were administered at mid-day. After 7 days of antibiotic therapy, the patient developed a mild fever that lasted for several days, which compared to a Jarish Herxheimer reaction. Because of an elevated ALT and AST, the azathioprine was discontinued 7 months after day 1. The patient responded favorably to the antibiotics for about 8 months, but by 13 months after day 1, he became symptomatic and relapsed. The period of relapse lasted from 13 months after day 1 to 1 year, 10 months after day 1 and during this time he remained on low dose antibiotics. A colonoscopy on 1 year, 8 months after day 1 showed multiple aphthous ulcers in the colon and his weight on that day was 77.3 pounds (35 kg). Two days later, a short course of prednisone was initiated at a dose of 10 mg/d and another two days later, the dose of prednisone was increased to 20 mg/d. By 1 year, 9 months after day 1, his weight was 90 pounds (41 kg).

Around 1.5 years after day 1, in addition to receiving antibiotics, over the course of a three-month period, the patient received a total of 11 once weekly ultraviolet blood irradiation (UVBI) treatments. A predecessor AVIcure Hemomodulator UVBI device was used.

In addition to UVBI therapy, the doses of clarithromycin and rifabutin were increased and ciprofloxacin was added to the regimen. Eight months, 2 days after day 1, the patient was started on ciprofloxacin at a dose of 125 mg taken twice per day (7 mg/kg per day) and two weeks later this dose was increased to 250 mg taken twice per day (14 mg/kg per day). Nine months, 1 day after day 1, when the patient weighed 90 pounds (41 kg) the dose of clarithromycin was increased to 750 mg, 500 mg taken in the a.m. and 250 mg taken in the p.m. (18 mg/kg per day) and the dose of rifabutin was increased to 450 mg taken 150 mg in the a.m. and 300 mg in the p.m. (11 mg/kg per day). A year after day 1, after the patient was in clinical remission, clofazimine (an antibiotic with restricted use in the United States which is used for the treatment of leprosy and *Mycobacterium avium* complex) was added at a dose of 50 mg taken once daily.

The patient had a history of seasonal asthma (triggered by pollen) beginning at age 3 years and the last episode of asthma he has experienced was 11 months after day 1.

The doses above for this patient were adjusted over time. He received over 4 years of continuous antibiotic therapy until 4 years, 8 months after day 1. From 4 years, 8 months after day 1, he was on cycled therapy of rifabutin, ciprofloxacin, and clarithromycin until 7 years after day 1. The patient has been in complete remission since 1 year, 11 months after day 1.

Since 7 years after day 1, he has received no medications of any type and he has been without any signs or symptoms of Crohn's disease and is now 5 feet 10.5 inches and 185 pounds (84.1 kg). A follow-up blood culture for MAP at 3 years, 2 months after day 1 failed to recover MAP by culture or detect MAP DNA by Polymerase Chain Reaction (PCR) and he tested negative for anti-MAP antibody. Currently, he has a normal blood count and is negative for inflammatory markers including ESR and CRP. A colonoscopy and upper gastrointestinal endoscopy in 10 years, 3 months after day 1 were normal.

Example 2

Less than a year before day 1 (in which MAP testing was performed as provided in Table 1), a 23-year-old female, the sibling of the patient of Example 1, began experiencing symptoms initially thought to be carpal tunnel syndrome and by three months before day 1, developed Raynaud's phenomenon in both hands. She had a several year history of hypothyroidism and was on thyroid hormone replacement. The symptoms of neuralgia and paresthesia progressively advanced and involved her bilateral hands, elbows, shoulders, neck, legs and feet. Less than a month after day 1, she was found to have Raynaud's phenomenon in both hands and the purple color change and cold temperature was profound.

Her workup included a normal EMG study, normal CT scan of the brain, and normal values for procalcitonin, ESR, CRP, IL-6, ASCA IgA and IgG, rheumatoid factor, ANA, SS-A/RO, SS-B/LA, SCL, RNP, SM, CCP, JO-1, Centromere antibodies, Anti-Hu TTGIgA, lyme serology, gliadin peptide IgA and IgG, antiendomysial IgA, serum MPA IgG, MPA IgA, MPA IgM, MPA kappa, MPA lambda, MPA kappa/lambda ratio, glutamic acid decarboxylase antibody and ganglioside antibody studies. Because of a history of travel to Guatamala 5 years prior to the onset of her illness, the patient's blood was tested for antibody to *M. leprae*. The PGL-1 assay was negative. The initial diagnosis was hypersensitivity syndrome and she also received the diagnosis of thoracic outlet syndrome with probable evolving complex regional pain syndrome (CRPS).

Recommendations for therapy included physical therapy, muscle relaxants and gabapentin. Gabapentin at the lowest recommended dose made her very dizzy and she therefore discontinued this medication. The patient obtained multiple sessions of physical therapy which were beneficial and engaged in gradually increasing regular exercise, including walking and swimming as tolerated. At 1 month after day 1, she could only walk 300 feet or tread water wearing a floatation device for 5 min. The cause of this condition is unknown.

Due to suspicion that CRPS could be a manifestation of a MAP infection, blood samples were tested for evidence of MAP infection. The first blood sample was obtained on day 1 and the second 2 weeks after day 1. The results of the MAP ELISA assays from both samples showed significantly elevated titers, S/P values of 1.24 and 1.31 respectively. The MAP PCR tests were both negative. MAP was detected by culture from the second blood sample. There was rapid progression of clinical disease between day 1, when her MAP antibody titer was 1.24 and the organism could not be cultured while she had monocytosis and lymphocytosis, and 2 weeks after day 1, when her antibody titer increased to 1.31 and the organism could now be cultured while she no longer had monocytosis and lymphocytosis. During this two week period she developed generalized extreme hypersensitivity to minor tactile stimuli. MAP experts were consulted and appropriate antibiotics were prescribed.

Other diagnostic test results included elevated cryoglobulins of 57 (normal 0-50 ug/mL) and ACE level of 59 (normal 8-53 U/L). Cryoglobulins and ACE are elevated in other mycobacterial infections including tuberculosis and leprosy. Prior to the onset of disease and the initiation of therapy, the patient had persistent relative lymphocytosis and eosinophilia which was present as early as 15 years before day 1. Relative lymphocytosis has been described in tuberculosis.

Neurologic findings are not uncommon in CD. In addition, siblings of patients with CD are at much higher risk of developing CD than the general population.

Around a month after day 1, the patient was placed on anti-MAP therapy as described of this invention and supplementary Vitamin A and Vitamin D similar to that administered to her brother (Example 1). Her height and weight are 5 feet 9.5 inches and 150 pounds (68.2 kg), respectively, and her antibiotic doses were as follows: Clarithromycin 500 mg twice daily (15 mg/kg per day), rifampin 300 mg twice daily (9 mg/kg per day), levofloxacin 500 mg per day (7 mg/kg per day) and clofazimine 100 mg 3 times per week (4 mg/kg per week) were taken for about 2 years and 5 months. Four days after the initiation of therapy she experienced a mild fever which lasted two days. She was administered 12 UVBI treatments at once weekly intervals for 3 months from 2 months after day 1 through about 5 months after day 1.

Following the initiation of therapy, she developed monocytosis and the relative lymphocytosis persisted. Since that time, she has shown marked clinical improvement including disappearance of the generalized hypersensitivity, disappearance of the previously grossly visible Raynaud's phenomenon in her hands, and improved ability to perform motor skills with a reduction in reported pain. By about 1 year and 10 months after day 1, she could swim one mile or walk five miles per day. Although her general condition has greatly improved including absence of the generalized extreme hypersensitivity, she still experiences episodes of migratory pain. With treatment of leprosy, reversal reactions and prolonged neuralgia have been observed. Six weeks after beginning the anti-MAP therapy of this invention, while still taking supplemental thyroxine, she began experiencing palpitations and it was noted that her TSH had dropped to the low normal range. On the presumption that the palpitations indicated that her thyroid function was recovering, two months after day 1 she stopped supplemental thyroxine, has not experienced symptoms of hypothyroidism, and her TSH is now in the normal range. A TSH from 6 months, 1 day after day 1 was 4.06 µIU/mL (reference range 0.350-5.55 µIU/mL). An ACE level from 6 months, 1 day after day 1 was still elevated at 58 U/L and a complete blood count from the same day was normal except for mild monocytosis of 9.3% (reference range 0%-8%) and eosinophilia of 9.5% (reference range 0%-4%). By 1 year, 11 months, 8 days after day 1, a complete blood count and differential were normal. After four months of therapy (at 5 months, 1 day after day 1), a follow-up blood culture for MAP showed a minimally decreased MAP ELISA S/P value of 1.2, the MAP PCR test was negative and MAP could not be cultured from this sample. A follow-up cryoglobulin study obtained from 5 months, 11 days after day 1 was negative after 4 hours and positive after 72 hours.

Example 3

Since two siblings (Examples 1 and 2 above) had evidence of MAP infections and responded to anti-MAP therapy of this invention, other relatives were tested. The paternal uncle of the patients from Examples 1 and 2, who has longstanding T1DM, is also infected with MAP. In addition, the uncle was found to have elevated ASCA IgA, a serologic marker, which is present in T1DM and CD. The uncle's MAP serum antibody S/P value was 0.49 (negative). The patient has declined treatment for MAP.

Example 4

The father of the patients of Examples 1 and 2 was tested for MAP infection on day 1. After 6 months of incubation, MAP was grown from his blood. His MAP PCR on PBMCs was negative and his MAP ELISA antibody S/P value was 0.15 (negative). He is healthy but suffered from seasonal asthma (triggered by pollen) at age 12 years and also while living in Germany for three years. In addition, he has rosacea, which was diagnosed by clinical signs and a skin biopsy showing non-caseating granulomas. This condition is treated with a topical ointment containing azelaic acid. 9 years before day 1, his blood was found positive for antibodies to p35 and p36 MAP antigens.

Because of the devastating nature of the diseases in Examples 1 and 2 and the poor record of efficacy, standard therapies were eschewed. Institutional review board (IRB) approval was not sought since the law allows off label use of FDA approved drugs and also allows the administration of UVBI in the resident state of the patient. IRB approval is generally not required in the care of individual patients. In Examples 1 through 3, infectious disease specialists were consulted and informed about the elevated MAP ELISA antibody titers and/or positive MAP cultures but declined to make recommendations regarding therapy.

Additional family members were tested for evidence of MAP infection as well. The mother of the patients from Examples 1 and 2 was negative for MAP by PCR on PBMC and culture, and had an ELISA S/P of 0.08 (negative). The brother of the patients from Examples 1 and 2 had a negative MAP PCR and negative culture and ELISA S/P of 0.59

(slightly elevated). The maternal grandfather of the patients from Examples 1 and 2 had a negative MAP PCR on PBMCs and negative culture and an ELISA S/P of 0.13 (negative). The maternal grandmother (with hypothyroidism) of the patients from Examples 1 and 2 had a negative MAP PCR on PBMCs and negative MAP culture and an ELISA S/P of 0.0 (negative). The families of both parents of the patients from Examples 1 and 2 have a history of susceptibility to mycobacterial infection.

In Example 1, the recovery of viable MAP in the setting of two diseases, Crohn's disease and asthma, and the failure to recover viable MAP in the absence of the diseases points to the pathogenic role of MAP in autoimmune diseases. Similarly, in Example 2, the recovery of viable MAP in the setting of two other diseases, complex regional pain syndrome and hypothyroidism, and the failure to recover viable MAP in the absence of these two other diseases also points to the pathogenic role of MAP. Furthermore, in Example 2, the recovery of the viable MAP in a case in which the patient suffered from complex regional pain syndrome cannot be explained by the leaky bowel hypothesis since this patient has not experienced bowel related symptoms. In addition, a pathogenic role of MAP in the human host is likely, considering the zoonotic capacity of slow-growing mycobacteria and because this organism is an obligate pathogen, i.e., one that does not propagate in the environment.

It is believed that the profound long lasting clinical remission in Example 1 resulted from anti-MAP therapy and is unlikely due to steroid administration, since such remissions rarely result from steroid administration alone.

In Examples 1 and 2, the rapid progression of the disease accompanied by an increase in antibodies to MAP antigens between the first two specimens may mirror Johne's disease in dairy cattle in which the progression in the severity of disease and the degree of mycobacterial colonization coincides with a switch from the TH1 to TH2 type immune response.

The presence of the viable bacterium in the blood of an apparently healthy host (Example 4) supports that apparently healthy individuals may have less virulent forms of disease such as transient childhood asthma or rosacea as noted in Example 4. In addition, if MAP-infected people are followed over a long enough period of time, some may eventually develop one of the diseases traditionally considered autoimmune.

UVBI may be beneficial in treating MAP causing one or more autoimmune diseases because ultraviolet light in the C region (UVC) inactivates bacterial and viral pathogens, present in the blood, which is irradiated. In the case of bacteria and DNA viruses, UVC induces the formation of thymine-thymine dimers, which prevents replication. In the case of RNA viruses, UVC induces the formation of uracil-uracil dimers which also prevents replication. Bacteria including *Mycobacterium tuberculosis* have UV repair mechanisms and normal lymphocytes also have UV repair mechanisms.

Because only 200 cc of blood in an average adult (or 4% of the total 5.0 liter blood volume) is treated during a single UVBI session, factors other than pathogen inactivation are likely to explain the potential benefit. Ultraviolet light shined on murine fibroblasts results in the formation of hydrogen peroxide and hydroxyl radicals which are also bactericidal and virucidal. Ultraviolet light in the A region and at higher doses and exposure durations causes immune suppression, but ultraviolet light in the B (UVB) region and UVC have been shown to stimulate dendritic cells. Hemoglobin which has been irradiated with UVB and UVC wavelengths exhibits fluorescence and the wavelength of light which is emitted, 365 nm, causes the formation of DNA or RNA adducts in riboflavin and other chromophores and these adducts are bactericidal and virucidal. It is now known that in spite of long term treatment of tuberculosis by antibiotics, there are persisters, which are not killed by the drugs. Also *Mycobacterium avium* complex organisms can resist the bactericidal activity of clarithromycin within the phagosomes of macrophages. Viable MAP organisms which have survived the antibiotics by either of these routes and which are within macrophages may not survive ultraviolet irradiation.

Vitamin D has been shown to play an important role in the host immune response to mycobacterial infection. Vitamins A and D have been shown to inhibit the growth of MAP in vitro. Vitamin D has also been shown to reduce the proliferation of *M. tuberculosis* in macrophages. Activated dendritic cells are known to produce Vitamin D and Vitamin D induces the intracellular production of cathelicidin, which is an antimicrobial protein. High levels of Vitamin D have been correlated with a reduced risk of developing multiple sclerosis, and Vitamin D intake is inversely associated with rheumatoid arthritis (another autoimmune condition) and the severity of this latter disease also correlates with Vitamin D levels. Finally, many types of cells including leukocytes and, in particular, monocytes, exposed to ultraviolet light secrete heat shock proteins and these proteins play an important role in the response to infection.

The combination of UVBI and antibiotics of this invention are believed to be synergistic in the treatment of autoimmune diseases targeting *Mycobacterium avium* subspecies *paratuberculosis* (MAP), as the combination yields more beneficial results than would be predictable from the additive effects of each. In certain circumstances, however, UVBI treatment without antibiotics may be used as provided herein. The autoimmune disease conditions are expected to be lifelong, and yet complete resolution of these diseases symptomatically and from the standpoint of negative blood cultures and MAP antibody studies may occur from the combination of UVBI and antibiotics of this invention.

The treatment of the above diseases by the above methods is not heretofore known. Currently, none of the above "autoimmune diseases" is recognized by the medical community as an infectious disease. Rather, the theory is largely ridiculed by most physicians who are the thought leaders of gastroenterology and infectious disease.

In various embodiments, the method or composition such as described above in embodiments for treating MAP may be directed to treating a patient having *Mycobacterium avium* complex (MAC) (as opposed to specifically MAP) causing one or more diseases. Thus, in any of the embodiments above, the method or corn position may be directed to treating MAC, such as, for example, species *M. avium* or *M. intracellulare* (also collectively previously referred to as *Mycobacterium avium-intracellulare* (MAI)), or such as MAP.

Thus, for example, in various embodiments, a method of treating a patient having *Mycobacterium avium* complex (MAC) causing one or more diseases includes: administering to the patient an effective amount of one or more antibiotics; and administering to the patient an effective amount of ultraviolet blood irradiation (UVBI) treatment. In that method, in one embodiment the one or more antibiotics include one or more of clarithromycin, azithromycin, rifampicin, rifabutin, clofazimine, ciprofloxacin, and metronidazole. In another embodiment, the method further includes administering to a patient at least one of Vitamin A and Vitamin D.

In an embodiment of the method for treating a patient having MAC causing one or more diseases, the one or more antibiotics include clarithromycin. In another embodiment, the one or more antibiotics further include at least one of rifabutin and rifampin. In another embodiment, the one or more antibiotics further include ethambutol.

In another embodiment of a method of treating a patient having *Mycobacterium avium* complex (MAC) causing one or more diseases such as described above, the method may include administering to a patient an effective amount of ultraviolet blood irradiation (UVBI) treatment and taking repeated measurements of MAC in the patient to demonstrate eradication of the MAC in the patient.

One embodiment of a composition for treating a patient having *Mycobacterium avium* complex (MAC) causing one or more diseases includes: an effective amount of one or more antibiotics; and an effective amount of ultraviolet blood irradiation (UVBI) treated blood of the patient. In an embodiment, the one or more antibiotics comprise one or more of clarithromycin, azithromycin, rifampicin, rifabutin, clofazimine, ciprofloxacin, and metronidazole. In an embodiment, the composition further includes at least one of Vitamin A and Vitamin D.

In an embodiment of the composition for treating a patient having *Mycobacterium avium* complex (MAC) causing one or more diseases, the one or more antibiotics include clarithromycin. In an embodiment, the one or more antibiotics further include at least one of rifabutin and rifampin. In an embodiment, the one or more antibiotics further include ethambutol.

Another embodiment of a composition for treating a patient having *Mycobacterium avium* complex (MAC) causing one or more diseases such as described above includes an effective amount of ultraviolet blood irradiation (UVBI) treated blood of the patient.

While specific embodiments of the invention have been described in detail, it should be appreciated by those skilled in the art that various modifications and alternations could be developed in light of the overall teachings of the disclosure. Accordingly, the particular arrangements, apparatuses, compositions, systems, and methods disclosed are meant to be illustrative only and not limiting as to the scope of the invention.

What is claimed is:

1. A composition for treating a patient having *Mycobacterium avium* subspecies *paratuberculosis* (MAP) causing one or more autoimmune diseases, comprising: an effective amount of one or more antibiotics; and an effective amount of ultraviolet blood irradiation (UVBI) treated blood of the patient.

2. The composition of claim 1, wherein the one or more antibiotics comprise one or more of clarithromycin, azithromycin, rifampicin, rifabutin, clofazimine, ciprofloxacin, and m etronidazole.

3. The composition of claim 2, further comprising at least one of Vitamin A and Vitamin D.

4. The composition of claim 1, wherein the one or more autoimmune diseases comprise one or more of Crohn's disease, ulcerative colitis, type 1 diabetes mellitus, multiple sclerosis, complex regional pain syndrome, hypothyroidism, idiopathic thrombocytopenic purpura, lymphangiomatosis, sarcoidosis, Sjogren's disease, myasthenia gravis, scleroderma, systemic lupus erythematosis, psoriasis, and fibromyalgia.

5. The composition of claim 1, wherein the one or more antibiotics comprise clarithromycin and rifabutin.

6. The composition of claim 5, wherein the one or more antibiotics further comprise clofazimine.

7. The composition of claim 1, wherein the one or more autoimmune diseases comprise complex regional pain syndrome.

8. The composition of claim 1, wherein the one or more autoimmune diseases comprise type 1 diabetes mellitus.

9. A composition for treating a patient having *Mycobacterium avium* subspecies *paratuberculosis* (MAP) causing one or more autoimmune diseases, comprising: an effective amount of ultraviolet blood irradiation (UVBI) treated blood of the patient.

10. A method of treating a patient having *Mycobacterium avium* subspecies *paratuberculosis* (MAP) causing one or more autoimmune diseases, comprising: administering to the patient a first effective amount of one or more antibiotics, the first effective amount of at least one or more antibiotics comprising a dose administered daily over a first period of between 1 year and 7 years; and concurrently administering to the patient an effective amount of ultraviolet blood irradiation (UVBI) treatment in at least 2 separate treatments, and optionally concurrently administering at least one steroid, wherein the method results in remission of at least one symptom of the one or more autoimmune diseases and prevents relapse of the symptom.

11. The method of claim 10, wherein the first effective amount of at least one or more antibiotics comprise one or more of clarithromycin, azithromycin, rifampicin, rifabutin, clofazimine, ciprofloxacin, and metronidazole.

12. The method of claim 11, further comprising administering to a patient at least one of Vitamin A and Vitamin D.

13. The method of claim 10, wherein the first effective amount of at least one or more antibiotics comprise clarithromycin.

14. The method of claim 13, wherein the first effective amount of at least one or more antibiotics further comprise at least one of rifabutin and rifampin.

15. The method of claim 14, wherein the one or more antibiotics further comprise at least one of ciprofloxacin and levofloxacin.

16. The method of claim 10, wherein the one or more autoimmune diseases comprise one or more of Crohn's disease, ulcerative colitis, type 1 diabetes mellitus, multiple sclerosis, complex regional pain syndrome, hypothyroidism, idiopathic thrombocytopenic purpura, lymphangiomatosis, sarcoidosis, Sjogren's disease, myasthenia gravis, scleroderma, systemic lupus erythematosis, psoriasis, and fibromyalgia.

17. The method of claim 10, further comprising performing at least one of a blood culture for MAP, a Polymerase Chain Reaction test for MAP, and a test for MAP antibodies to confirm that the MAP has been eradicated in the patient.

18. The method of claim 10, wherein the one or more autoimmune diseases comprise Crohn's disease.

19. The method of claim 18, further comprising performing at least one of a blood culture for MAP, a Polymerase Chain Reaction test for MAP, and a test for MAP antibodies to confirm that the MAP causing the Crohn's disease has been eradicated in the patient.

20. The method of claim 18, wherein the first effective amount of at least one or more antibiotics comprise clarithromycin and rifabutin.

21. The method of claim 20, wherein the one or more antibiotics further comprise clofazimine, the clofazimine administered to the patient along with the other one or more antibiotics once the patient is in clinical remission for MAP.

22. The method of claim 10, wherein the one or more autoimmune diseases comprise complex regional pain syndrome.

23. The method of claim 22, wherein and the one or more antibiotics comprise clarithromycin, rifampin, ciprofloxacin, and clofazimine.

24. The method of claim 23, further comprising administering to the patient at least one of Vitamin A and Vitamin D.

25. The method of claim 22, further comprising performing at least one of a blood culture for MAP, a Polymerase Chain Reaction test for MAP, and a test for MAP antibodies to confirm that the MAP causing the complex regional pain syndrome has been eradicated in the patient.

26. The method of claim 10, wherein the one or more autoimmune diseases comprise type 1 diabetes mellitus.

27. The method of claim 10, wherein at least one UVBI treatment is administered at least 1 week before the step of administering a first effective amount of at least one or more antibiotics, and wherein at least 2 additional UVBI treatments are administered concurrently with the step of administering a first effective amount of at least one or more antibiotics, and wherein the method further comprises administering a second effective amount of at least one antibiotic for a second period comprising administering for at least 1 year after the remission of at least one symptom of the one or more autoimmune diseases.

28. The method of claim 27, wherein the step of administering to the patient a first effective amount of one or more antibiotics, the first effective amount of at least one or more antibiotics comprising a dose administered daily over a first period of between 2 years and 3 years, comprises at least one of 18 mg/kg per day of clarithromycin, 9 mg/kg per day of rifampin, 14 mg/kg per day of ciprofloxacin, and 7 mg/kg per day of levofloxacin, and wherein the step of concurrently administering to the patient an effective amount of ultraviolet blood irradiation (UVBI) treatment comprises at least 10 treatments of UVBI, and the step of concurrently administering at least one steroid comprises administering prednisone, and upon remission of at least one symptom of the one or more autoimmune diseases, the step of administering a second effective amount of at least one antibiotic for a second period of at least 1 year.

29. The method of claim 16, wherein at least one UVBI treatment is administered at least 1 week before the step of administering a first effective amount of at least one or more antibiotics, and wherein at least 2 additional UVBI treatments are administered concurrently with the step of administering a first effective amount of at least one or more antibiotics, and wherein the step of administering a second effective amount of at least one antibiotic for a second period comprises administering for at least 1 year after the remission of at least one symptom of the one or more autoimmune diseases.

30. The method of claim 16, wherein the step of administering to the patient a first effective amount of one or more antibiotics, the first effective amount of at least one or more antibiotics comprising a dose administered daily over a first period of between 2 years and 3 years, comprises at least one of 18 mg/kg per day of clarithromycin, 9 mg/kg per day of rifampin, 14 mg/kg per day of ciprofloxacin, and 7 mg/kg per day of levofloxacin, and wherein the step of concurrently administering to the patient an effective amount of ultraviolet blood irradiation (UVBI) treatment comprises at least 10 treatments of UVBI, and the step of concurrently administering at least one steroid comprises administering prednisone, and upon remission of at least one symptom of the one or more autoimmune diseases, the method further comprises administering a second effective amount of at least one antibiotic for a second period of at least one year.

* * * * *